United States Patent
Hu et al.

(10) Patent No.: US 9,498,510 B2
(45) Date of Patent: Nov. 22, 2016

(54) POLYPEPTIDE, NUCLEOTIDE SEQUENCE THEREOF, AND METHOD FOR USING THE SAME FOR PREVENTING DNA SYNTHESIS AND INHIBITING CELL PROLIFERATION

(71) Applicant: Wuhan Yicheng Biotech. Inc., Wuhan (CN)

(72) Inventors: Junbo Hu, Wuhan (CN); Xianmin Xia, Wuhan (CN); Guihua Wang, Wuhan (CN)

(73) Assignee: WUHAN YICHENG BIOTECH. INC., Wuhan (CN)

( * ) Notice: Subject to any disclaimer, the term of this patent is extended or adjusted under 35 U.S.C. 154(b) by 0 days.

(21) Appl. No.: 15/071,178

(22) Filed: Mar. 15, 2016

(65) Prior Publication Data
US 2016/0303183 A1     Oct. 20, 2016

Related U.S. Application Data

(60) Division of application No. 14/187,354, filed on Feb. 24, 2014, now abandoned, which is a continuation-in-part of application No. PCT/CN2012/078378, filed on Jul. 9, 2012.

(30) Foreign Application Priority Data

Aug. 23, 2011 (CN) .......................... 2011 1 0242869

(51) Int. Cl.
*A61K 38/00* (2006.01)
*A61K 38/16* (2006.01)
*C07K 7/08* (2006.01)

(52) U.S. Cl.
CPC *A61K 38/00* (2013.01); *C07K 7/08* (2013.01)

(58) Field of Classification Search
CPC .. A61K 38/00; A61K 38/16; C07K 2319/10; C07K 2319/60; C07K 7/08
USPC ...... 514/19.3, 19.6, 19.2; 530/326, 324, 325
See application file for complete search history.

(56) References Cited

U.S. PATENT DOCUMENTS

2008/0014598 A1*   1/2008   Wiederhold ........... C07K 16/40
                                                                              435/7.4
2009/0269351 A1*   10/2009   Phillips ................... A61K 31/00
                                                                              424/139.1

OTHER PUBLICATIONS

Q5T4P3 from UniProt.org, pp. 1-8. Integrated into UniProtKB and last sequence update on Dec. 21, 2004.*

* cited by examiner

*Primary Examiner* — Julie Ha
(74) *Attorney, Agent, or Firm* — Matthias Scholl, PC; Matthias Scholl

(57) ABSTRACT

A polypeptide represented by SEQ ID NO: 1 and a method for treatment of a tumor and another disease associated with abnormal cell proliferation are described. The method includes administering a pharmaceutically-effective amount of the polypeptide to a patient in need thereof.

1 Claim, 2 Drawing Sheets

G₀/G₁ 60.1%
S 23.5%
G₂/M 16.4%

G₀/G₁ 62.9%
S 22.3%
G₂/M 14.8%

G₀/G₁ 66.9%
S 19.6%
G₂/M 13.5%

G₀/G₁ 74.2%
S 10.5%
G₂/M 15.3%

SEQUENCE LISTING

```
<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: Fully synthetic peptide

<400> SEQUENCE: 1

Met Pro Tyr Ser Thr Glu Leu Ile Phe Tyr Ile Glu Met Asp Pro
1               5                   10                  15

<210> SEQ ID NO 2
<211> LENGTH: 26
<212> TYPE: PRT
<213> ORGANISM: Artificial Sequence
<220> FEATURE:
<223> OTHER INFORMATION: Fully synthetic peptide

<400> SEQUENCE: 2
```

```
Arg Asp Leu Tyr Asp Asp Asp Lys Asp Arg Met Pro Tyr Ser Thr
1               5                   10                  15

Glu Leu Ile Phe Tyr Ile Glu Met Asp Pro
            20                  25

<210> SEQ ID NO 3
<211> LENGTH: 61
<212> TYPE: DNA
<213> ORGANISM: Artificial Sequence
<220> FEATURE:
<223> OTHER INFORMATION: Fully synthetic single stranded DNA

<400> SEQUENCE: 3
ttttgaattc atgccctatt cgacagaact gatattttat attgaaatgg atcctggatc    60
c                                                                    61

<210> SEQ ID NO 4
<211> LENGTH: 61
<212> TYPE: DNA
<213> ORGANISM: Artificial Sequence
<220> FEATURE:
<223> OTHER INFORMATION: Fully synthetic single stranded DNA

<400> SEQUENCE: 4
ttttggatcc aggatccatt tcaatataaa atatctgttc tgtcgaatag ggcatgaatt    60
c                                                                    61

<210> SEQ ID NO 5
<211> LENGTH: 11
<212> TYPE: PRT
<213> ORGANISM: Artificial Sequence
<220> FEATURE:
<223> OTHER INFORMATION: Fully synthetic peptide

<400> SEQUENCE: 5

Arg Asp Leu Tyr Asp Asp Asp Lys Asp Arg
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Fully synthetic peptide

<400> SEQUENCE: 6

Asp Arg Arg Asp Leu Tyr Asp Asp Asp Lys Asp Arg Met Ala Gly
1               5                   10                  15

Thr Met
```

POLYPEPTIDE, NUCLEOTIDE SEQUENCE THEREOF, AND METHOD FOR USING THE SAME FOR PREVENTING DNA SYNTHESIS AND INHIBITING CELL PROLIFERATION

CROSS-REFERENCE TO RELATED APPLICATIONS

This application is a divisional of U.S. Ser. No. 14/187,354 filed on Feb. 24, 2014, now pending, which is a continuation-in-part of International Patent Application No. PCT/CN2012/078378 with an international filing date of Jul. 9, 2012, designating the United States, which is now abandoned as to the United States and is based on Chinese Patent Application No. 201110242869.3 filed Aug. 23, 2011. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

1. Field of the Invention

The invention relates to a polypeptide, a nucleotide sequence thereof, and a method for using the same for preventing DNA synthesis and inhibiting cell proliferation.

2. Description of the Related Art

With the disclosure of signaling transduction pathways, more and more tumor-targeting drugs have been developed. And some of them have been successfully applied in clinic and gotten good effects. For example, the protein BCR-ABL expressed in many leukemia cells, which has relatively strong protein kinase activity and plays an important role in the occurrence and development of leukemia. Through studying the structure of protein BCR-ABL, many compounds that can specifically inhibit the biological activity of protein BCR-ABL are designed and produced, for example, Glivec is used in treatment for leukemia.

Cell growth signals are transmitted to cell nucleus by growth-promoting factors inside and outside cells via a series of proteins, bringing about the change of structure and function of many regulatory cyclins and leading to cell division. Among these proteins regulating cell cycle, proliferating cell nuclear antigen (PCNA) plays a significant role. DNA replication fork is the key protein complex of DNA synthesis in DNA replication. PCNA is a composition of DNA replication fork complex and can bind DNA and many kinds of proteins, especially the DNA polymerase necessary for DNA replication, which facilitates DNA polymerase to synthesize new DNA chains. PCNA exists in all dividing cells. Because of PCNA's vital function in cell cycle, to block its biological function in cell cycle is a means to develop new drugs for treatment of tumor and other diseases resulting from abnormal cell proliferation. Till up to now, as the mechanism that PCNA takes part in cell cycle regulation is unknown, there is no useful method or compound that can directly block the biological function of PCNA to inhibit cell proliferation.

SUMMARY OF THE INVENTION

In view of the above-described problems, it is one objective of the invention to provide a polypeptide and a method for using the same for preventing DNA synthesis and inhibiting cell proliferation. The polypeptide in the invention has the biological function of preventing PCNA from binding DNA polymerase thereby inhibiting cell division, and can effectively inhibit the growth of tumors in animals.

To achieve the above objective, in accordance with one embodiment of the invention, there is provided a polypeptide preventing DNA synthesis and inhibiting cell proliferation, the polypeptide being represented by SEQ ID NO: 1: methionine-proline tyrosine-serine-threonine-glutamic acid-leucine-isoleucine-phenylalanine-tyrosine-isoleucine-glutamic acid-methionine-asparaginic acid-proline.

In accordance with another embodiment of the invention, there is provided a method for treatment of a tumor in a patient comprising administering to the patient a therapeutically-effective amount of the polypeptide.

The invention also provides an isolated polynucleotide comprising a nucleotide sequence encoding the polypeptide, the nucleotide sequence comprising a double stranded DNA comprising a first single strand represented by SEQ ID NO: 3 and a second single strand represented by SEQ ID NO: 4.

In accordance with still another embodiment of the invention, there is provided a method for treatment of a tumor in a patient comprising administering to the patient a therapeutically-effective amount of the isolated nucleotide.

The invention also provides a fused polypeptide PTD-P15 represented by SEQ ID NO: 2: arginine-asparaginic acid-leucine-tyrosine-asparaginic acid-asparaginic acid-asparaginic acid-asparaginic acid-lysine-asparaginic acid-arginine-methionine-proline-tyrosine-serine-threonine-glutamic acid-leucine-isoleucine phenylalanine-tyrosine-isoleucine-glutamic acid-methionine-asparaginic acid-proline.

The invention also provides a method for treatment of a tumor in a patient comprising administering to the patient a therapeutically-effective amount of the fused polypeptide PTD-P15.

In this research, the interaction between a polypeptide fragment and PCNA has been found. The amino acid sequence of the polypeptide is represented by SEQ ID NO: 1: methionine-proline-tyrosine-serine-threonine-glutamic acid-leucine-isoleucine-phenylalanine-tyrosine-isoleucine-glutamic acid-methionine-asparaginic acid-proline; hereinafter the polypeptide is called as P15. And it is also found that, after the binding of P15 & PCNA, the binding of PCNA & DNA polymerase is blocked, while the DNA polymerase bound on PCNA is necessary for DNA replication, an important process in cell cycle. According to this result, it is assumed that, if P15 is expressed in cells, the polypeptide can inhibit the binding of PCNA & DNA polymerase, further inhibiting the DNA replication mediated by DNA polymerase and preventing cell division.

The key to testify the above model is to introduce P15 into cells and observe the impact of P15 on cell division. To achieve the purpose, by virtue of molecular biological techniques, we created a DNA construction which codes the fused protein comprising P15 and green fluorescent protein (GFP), thereafter transferred the construction into cultured human cells, and then observed the change of expressed fuse protein P15-GFP in cell cycle. In addition, we produced a fused polypeptide PTD-P15 comprising a polypeptide fragment and P15 having the ability to penetrate cytomembrane. The amino acid sequence of PTD is represented by SEQ ID NO: 5: arginine-asparaginic acid-leucine-tyrosine-asparaginic acid-asparaginic acid-asparaginic acid-asparaginic acid-lysine-asparaginic acid-arginine. We added PTD-P15 in cultured cells and observed the impact of P15 into cells on cell cycle. To observe the impact of P15 on the growth of tumor in the animal model, we observed whether PTD-P15 could inhibit the growth of tumor in the animal model through injecting PTD-P15 into caudal vein of small mice.

The experiment results show that, when P15 is expressed in several kinds of cultured cell lines with growth and division abilities or PTD-P15 is added in, P15 will inhibit the ability of PCNA to bind DNA polymerase, causing a significant reduction in the observational index regarding DNA synthesis and other several ones testifying cell proliferation, which proves that P15 has the ability to inhibit cell proliferation; and the injection of PTD-P15 can inhibit cell proliferation and the growth of tumor in animal model.

Advantages of the invention are summarized as follows:

1) P15 has the ability to block PCNA from binding DNA polymerase, thus the DNA replication facilitated by DNA polymerase is inhibited, resulting in cell cycle arrest. This provides a new method and approach to design and screen new drugs for treatment of tumor and another disease resulting from abnormal cell proliferation. Simultaneously, PTD-P15 can effectively inhibit tumor growth. This proves that P15 still has the biological effect to inhibit cell proliferation even after penetrating cytomembrane, and also shows that polypeptides or molecules with the ability to penetrate cytomembrane can be used in helping P15 with biological activity to penetrate cytomembrane.

2) P15 has low toxic and side effects and weak antigenicity, and according to the experimental results, it is found that, without obvious impact on apoptosis, P15 has no obvious lethal effect on normal cells. When PTD-P15 is added into cultured cells or applied to animals, no obvious toxicity is observed.

3) Both P15 and PTD-P15 expressed in cells can effectively inhibit the growth of tumor cells of human beings and mice in vivo and vitro culture systems. This proves that P15 has advantages such as high efficiency and broad spectrum in treatment of tumor resulting from abnormal cell proliferation.

4) With small molecular weight, PTD-P15 can be chemically synthesized, and is convenient for direct large-scale application in clinic. And also, we can inject P15 into cells using other methods (e.g. the use of plasmid or virus vectors) to treat tumor resulting from abnormal cell proliferation.

DETAILED DESCRIPTION OF THE EMBODIMENTS

Figure 1:
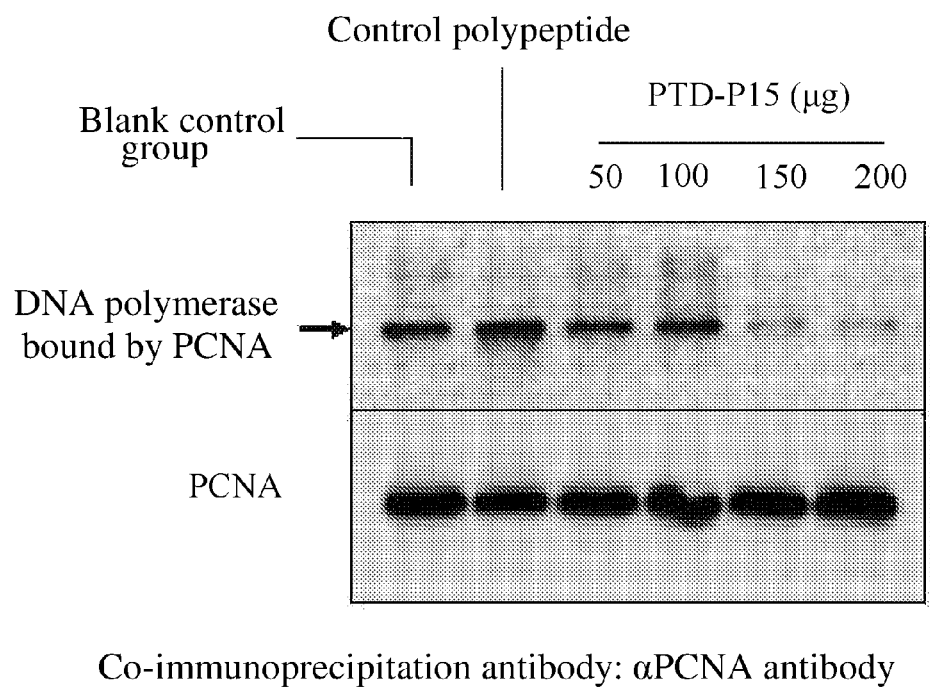
FIG. 1 shows PTD-P15 blocks PCNA from binding DNA polymerase. HT29 rectal cancer cells from patients were cultivated in culture dishes, into which the control polypeptide or different amounts of PTD-P15 were added. After a night of cultivation, cells were collected, and the amount of DNA polymerase bound by PCNA in cells was tested with co-imunoprecipitation. Results show that, the addition of PTD-P15 can reduce the DNA polymerase bound by PCNA, because the amount of DNA polymerase bound by PCNA is closely related with DNA replication. Thus, it is shown that, PTD-P15 can lower the speed of DNA replication. So long as the ability of PCNA to bind DNA polymerase is blocked, the function of the polymerase to facilitate DNA replication is inhibited, and cell division is blocked.
Figure 2A:
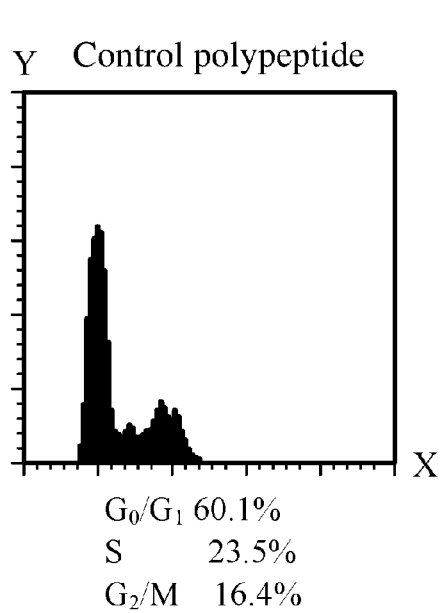
FIGS. 2A, 2B, 2C and 2D show different cell cycles inhibited by PTD-P15. HT29 rectal cancer cells from patients were cultivated in culture dishes, into which the control polypeptide or different amounts of PTD-P15 were added. After 24-hours of cultivation, cells were collected, and the percentage of cells in different cell cycles is tested. Results show that, PTD-P15 can increase amounts of cells in phase $G_0/G_1$, while decrease the amount of cells in phase S and $G_2/M$, which shows that PTD-P15 can inhibit cell cycle.
Figure 2B:
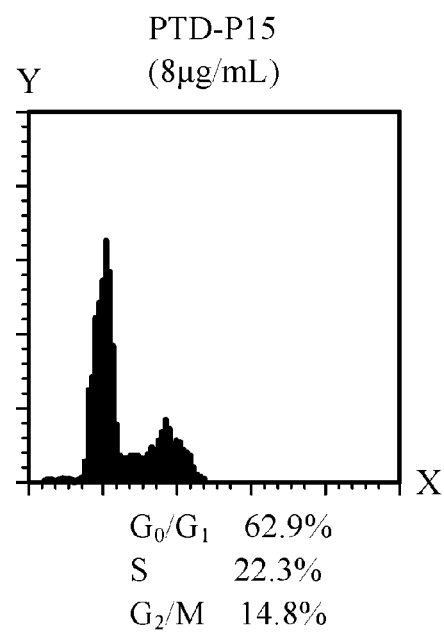
Figure 2C:
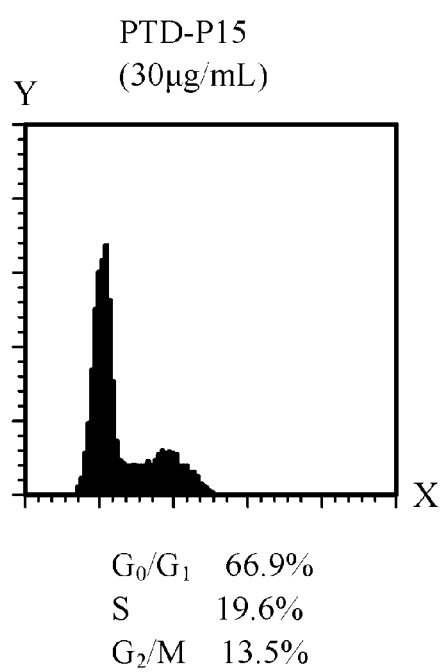
Figure 2D:
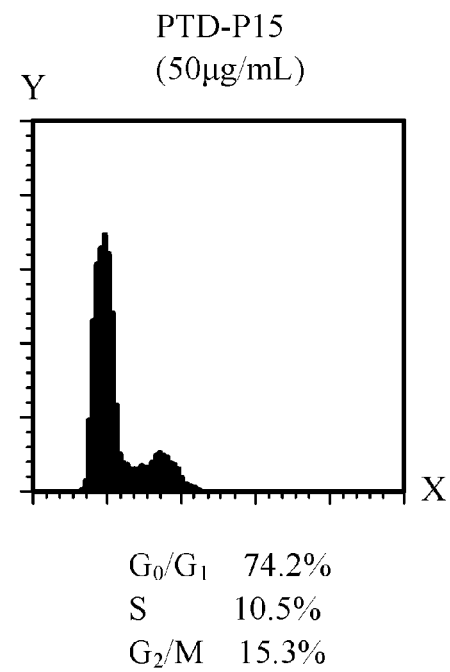

For further illustrating the invention, experiments detailing a polypeptide and a method for using the same for preventing DNA synthesis and inhibiting cell proliferation are described below. It should be noted that the following examples are intended to describe and not to limit the invention.

Example 1 Test of Expression of P15-GFP by DNA Construction after cDNA Coding P15 Introduced into pEGFP Vector pEGFP-N, 1 was purchased from American Clontech (Cat No. 6085-1). The plasmid including cDNA that can code GFP was digested with EcoRI-BamHI (purchased from American Promega, Cat No. R6011, R6021), and then the digested plasmid was separated and purified in agarose gel for future coupled reaction. The reagent kit used for DNA fragment recovery was purchased from German Qiagen (Cat No. 28704).

The cDNA coding P15 was from double stranded DNA by means of artificial synthesis, comprising:

Single strand 1 represented by SEQ ID NO: 3

5'TTTTGAATTCATGCCCTATTCGACAGAACTGATATTTTATATTGAAAT

GGATCCTGGATCC;

and

Single strand 2 represented by SEQ ID NO: 4

5'TTTTGGATCCAGGATCCATTTCAATATAAAATATCTGTTCTGTCGAAT

AGGGCATGAATTC.

After mixed, the two single strands combined into double stranded DNA. After purification (the reagent kit used for purification purchased from German Qiagen, Cat No. 28704), the outcome was digested with EcoRI-BamHI first; and purified with agarose gel, then brought to coupled reaction with the carrier pEGFP-N1 after digest and purification (the reagent kit used for coupled reaction purchased from American Promega, Cat No. M1801). After bacterial transformation (competent cell from American Promega, Cat No. L2001, positive clones were picked out. After the correctness of the sequence of cDNA was proven through nucleotide sequence testing, the prepared plasmid was purified on a large scale (the reagent kit used for large-scale purification purchased from German Qiagen, Cat No. A7270) for future experiments. This plasmid expressed one fused protein consisted of P15 and GFP respectively in eukaryotic cells. The expressed P15 was connected to the end N of GFP and the fused protein was called as P15-GFP.

The reagent kit for transfection was purchased from American Invitrogen (Cat No. 11668). The transfection experiment was finished according to instructions provided by the manufacturer. Cells COS7 were cultured in a DMEM of beef serum with a mass concentration of 10%. After transfected for 48 hours, the Cells COS7 were washed twice with PBS. Next lysate was added for cell lysis. After DNA was damaged with ultrasonic wave, appropriate amounts of 2-mercaptoethanol and bromophennol blue were added.

After disposed in boiling water for 5 minutes and stored on ice, sample was taken out and added into SDS-polyacrylamide gel with a mass concentration of 12% for electrophoresis. The separated protein was transferred to nylon membrane, through which the generation of fused protein was tested with anti-GFP antibody (purchased from American Invitrogen, Cat No. R970), and the results proved the expression of P15-GFP in cells.

Example 2 Experiment of Inhibiting Cell Proliferation and Cell Cycle by Expression of P15

The impact of P15 on cell proliferation is tested with NIH/3T3 (fibroblast and eptithlial cells, purchased from American ATCC, Cat No. CRL-1658) and MCF-7 (breast cancer cell line, purchased from American ATCC, Cat No. HTB-22). The cells were cultured in a 10 cm cell culture dish containing a DMEM of 10% fetal beef serum (SBF) with a mass concentration of 10% at 37° C. under a condition of 5% $CO_2$ (volume)/95% air (volume).

Plasmid used for experiment: pEGFP-P15 (to express fused protein P15-GFP); control plasmid: pEGFP-N1

After the plasmid for transfection and the lipofectamine reagent (purchased from American Invitrogen, Cat No. 11668) were mixed, the mixture stayed for 15 minutes at room temperature. Then the mixture was first introduced into cells (with a cell density of about 50%) cultured in DMEM without serum for 5 hours of cultivation at 37° C. and next into SBF with a mass concentration of 10% for 48 hours of cultivation. Under fluorescence microscope, it was easy to distinguish the cells that express fused GFP and single fluorescent proteins and the ones that do not express these proteins. In addition, by the use of FCM, it was easy to separate and purify the positive fluorescent protein cells. The symbolic indicators to test cell proliferation such as cell cycle were used to study and testify the impact of P15 on cell proliferation, while in these experiments, only the cells that express fluorescent proteins were used as control group.

First, we used the above mentioned plasmid to transfect 3T3 and MCF7, and used FCM to sort the positive GFP cells transfected with DNA and analyzed the cycle distribution of these cells two days later.

The experimental results show that: the expression for P15 has no obvious impact on cell apoptosis, while P15 can inhibit cell cycle from stepping in Phase S and inducing cells into Phase G0/G1, as shown in Table 1.

TABLE 1

| Functions of P15 in inhibiting cell cycle and inducing cells into Phase G0/G1 | | | | | |
|---|---|---|---|---|---|
| | Cells 3T3 | | | Cells MCF7 | |
| | $G_0/G_1$ | S | $G_2/M$ | $G_0/G_1$ | S | $G_2/M$ |
| GFP | 32.4% | 25.9% | 41.7% | 62.2% | 22.6% | 15.2% |
| P15-GFP | 52.1% | 22.1% | 25.7% | 85.6% | 11.1% | 3.3% |

DNA synthesis is the symbol of cell proliferation. In the next experiment, we tested the impact of P15 on DNA synthesis. Within the 15 hours after 3T3 and MCF7 transfecting pEGFP-N, 1 and expressing P15-GFP plasmid for two days, the BrdU labeled cells that can penetrate in the newly synthesized DNA chain were added in cell culture fluid. The positive GFP cells in plasmid were detected and transfected with immunofluorescence technique, and the positive rate of BrdU penetration in DNA (this reflects the rate of DNA synthesis) was ascertained. The results show that, P15 also strongly inhibited the synthesis of DNA (shown in Table 2).

TABLE 2

| P15 inhibiting DNA synthesis | | | | |
|---|---|---|---|---|
| | Cells 3T3 | | Cells MCF7 | |
| | Positive BrdU cells | Inhibition ratio | Positive BrdU cells | Inhibition ratio |
| GFP | 53.8% | 0% | 31.2% | 0% |
| P15-GFP | 12.5% | 76.8% | 5.2% | 83.4% |

Example 3 Artificial Synthesis of Fused Polypeptide PTD-P15 Comprising Polypeptide and P15

In fact, P15 cannot freely penetrate cell membrane. To observe the impact of P15 on cell cycle and tumor growth, we artificially synthesized P15-fused polypeptide that can penetrate cell membrane. The fused one was called as PTD-P15 represented by SEQ ID NO: 2: arginine-asparaginic acid-leucine-tyrosine-asparaginic acid-asparaginic acid-asparaginic acid-asparaginic acid-lysine-asparaginic acid-arginine-methionine-proline-tyrosine-serine-threonine-glutamic acid-leucine-isoleucine phenylalanine-tyrosine-isoleucine-glutamic acid-methionine-asparaginic acid-proline. The amino acid sequence of the fragment P15 is represented by SEQ ID NO: 1: methionine-proline-tyrosine-serine-threonine-glutamic acid-leucine-isoleucine-phenylalanine-tyrosine-isoleucine-glutamic acid-methionine-asparaginic acid-proline; and the fragment of PTD with the function to penetrate cell membrane is represented by SEQ ID NO: 5: arginine-asparaginic acid-leucine-tyrosine-asparaginic acid-asparaginic acid-asparaginic acid-asparaginic acid-asparaginic acid-lysine-asparaginic acid-arginine.

In the meanwhile, we designed and synthesized a control polypeptide represented by SEQ ID NO: 6: asparaginic acid-arginine-arginine-asparaginic acid-leucine-tyrosine-asparaginic acid-asparaginic acid-asparaginic acid-asparaginic acid-lysine-asparaginic acid-arginine-methionine-alanine-glycine-threonine-methionine.

Example 4 PTD-P15 Blocking PCNA Binding DNA Polymerase

PTD-N15 blocks PCNA binding DNA polymerase. Human rectal cancer cells HT29 were cultured in culture dishes, into which the control polypeptide or different amounts of PTD-P15 were added. After a night of culture, cells were collected, and the amount of DNA polymerase bound by PCNA in cells was tested with co-immunoprecipitation. The results show that, the addition of PTD-P15 CAN reduce the DNA polymerase bound by PCNA, because the amount of DNA polymerase bound by PCNA is closely related with DNA replication. In this connection we can say that, PTD-P15 can lower the speed of DNA replication. So long as PCNA is blocked from binding DNA polymerase, the function of the polymerase to facilitate DNA replication is inhibited, and cell division is blocked (as shown in FIG. 1).

Example 5 Experiment of the Impact of Fused Polypeptide PTD-P15 on Cell Proliferation and Cycle The impact of PTD-P15 on cell proliferation was tested with human HeLa cell line (Hela cells purchased from American ATCC, Cat No. HTB-22). Hela cells were cultured in 10 cm cell culture dishes containing a DMEM of 10% fetal beef serum (SBF) with a mass concentration of 10% at 37° C. under an air culture condition of 5% $CO_2$ (volume)/95% air (volume). When the cells were cultured till to the logarithmic phase, PTD-P15 in different concentrations (respectively 8, 30 and 50 mcg/mL) were added, while control polypeptide (blank control group) was added in other cultured cells for control. After 24-hours of culture, cells were collected and FCM was adopted for cell cycle analysis. The experimental results show that: PTD-P15 can inhibit cell proliferation, increase amounts of cells in phase $G_0/G_1$ while has no obvious impact on cell apoptosis, as shown in FIGS. 2A, 2B, 2C and 2D.

Example 6 Experiment of PTD-P15 Inhibiting the Growth of Human Rectal Cancer Tumor in Mice After $5\times10^6$ human rectal cancer cells HT29 injected into the subcutaneous tissue of mice, the mice were randomly divided into two groups. After one day from the injection of the tumor cells, several 1 mg of PTD-P15 were injected into the mice in the treatment group via caudal vein, and the injection of the same amount was repeated every other day for five times. The injection times and time of 1 mg of control polypeptide were as the same as those for the treatment group. After ten days from the injection of tumor cells, the mice were killed, from which tumors were taken out for weight measurement. The results show that: compared with the control group, the weight of the tumors in the mice treated with PTD-P15 was reduced by 57%.

Example 7 Experiment of PTD-P15 Inhibiting the Growth of Human Leukemia Tumor in Mice After $5\times10^6$ human granulocytic leukemia cells K562 injected into the subcutaneous tissue of mice, the mice were randomly divided into five groups. Mice in each group were respectively injected with 1 mg of blank solution, 1 mg of control polypeptide, 1 mg of PTD-P15, 10 mcg of Glivec and the solution comprising 1 mg of PTD-P15÷10 mcg of Glivec, and the injection of the same amounts was repeated every other day for 7 times. After two weeks, the mice were killed, from which the tumors grown in the subcutaneous tissue of the mice were taken out and weighed. The results show that, compared with the control group, the injection of PTD-P15 can obviously reduce the weight of the tumors produced by K562 by 34%. Glivec is a medicine used for leukemia in clinic at present, and in the present, the injection of Glivec also reduced the weight of tumors by 48%. In case of the combination of PTD-P15 and Glivec, there was greater reduction in the weight of tumors than that of the tumors produced providing that only one of the two drugs was injected individually, and the reduction could be 69% when compared with the control polypeptide control. This proves that, the combination of PTD-P15 and Glivec has better tumor treatment effect than individual injection of them has, as shown in Table 3.

TABLE 3

PTD-P15 inhibiting the growth of tumor formed in cells K562 in animal model

| Animal group | Average weight of tumors (g) | Inhibition ratio |
|---|---|---|
| Blank control | 2.48 | 0% |
| Control polypeptide | 2.53 | −2% |
| PTD-P15 (1 mg) | 1.63 | 34% |
| Glivec (10 mcg) | 1.28 | 48% |
| PTD-P15 (1 mg) + Glivec (10 mcg) | 0.76 | 69% |

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for treatment of rectal cancer or leukemia in a patient in need thereof, the method comprising administering to the patient a therapeutically-effective amount of a polypeptide, wherein the polypeptide comprises the amino acid sequence consisting of SEQ ID NO: 1.

* * * * *